US00PP29533P3

(12) United States Plant Patent
Radler

(10) Patent No.: US PP29,533 P3
(45) Date of Patent: Jul. 24, 2018

(54) CLIMBING ROSE PLANT NAMED 'RADWIRE'

(50) Latin Name: *Rosa hybrida*
Varietal Denomination: Radwire

(71) Applicant: The Conard-Pyle Company, West Grove, PA (US)

(72) Inventor: William J. Radler, Greenfield, WI (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/530,095

(22) Filed: Dec. 2, 2016

(65) Prior Publication Data

US 2018/0160578 P1 Jun. 7, 2018

(51) Int. Cl.
*A01H 5/02* (2018.01)

(52) U.S. Cl.
USPC ..... Plt./114
CPC ..... *A01H 5/0222* (2013.01)

(58) Field of Classification Search
USPC ..... Plt./114, 115, 137, 138, 139, 149, 109
CPC ..... A01H 5/0222; A01H 5/02; A01H 5/00
See application file for complete search history.

(56) References Cited

PUBLICATIONS

Kempinger-Demski Journal Sentinel Mar. 26, 2016, retrieved on Nov. 30, 2017, retrieved from the Internet at https://www.jsonline.com/story/life/home-garden/garden/2016/03/27/new-varieties-of-plants-ready-to-brighten-yards/84933704/, 6 pp. (Year: 2016).*

* cited by examiner

*Primary Examiner* — June Hwu
(74) *Attorney, Agent, or Firm* — Buchanan Ingersoll & Rooney, PC

(57) ABSTRACT

A new and distinct variety of climbing rose plant herein referred to by its cultivar name, 'Radwire', is provided which forms in abundance on a substantially continuous basis attractive, cup-shaped, deep pink blossoms. The vegetation is vigorous and the growth habit is very bushy and climbing. Attractive, semi-glossy, medium green foliage is formed. Excellent disease resistance is exhibited, particularly for black spot, rust, and mildews. The new variety is particularly well suited for growing as distinctive ornamentation in the landscape.

1 Drawing Sheet

Botanical/commercial classification: *Rosa hybrida*/ Climbing Rose Plant.

Varietal denomination: cv. Radwire.

SUMMARY OF THE INVENTION

The new variety of *Rosa hybrida* Climbing rose plant of the present invention was created in June 2006 at Greenfield, Wis., U.S.A. The seed that produced the new variety of climbing rose plant was from mixed parents of unreleased and unnamed breeding parents (each non-patented in the United States). No further definitive information concerning the identity of the parents is available.

The seeds resulting from the above pollination were sown and small plants were obtained which were physically and biologically different from each other. Selective study resulted in the identification of a single plant of the new variety.

It was found that the new Climbing rose plant of the present invention possesses the following combination of characteristics:

(a) abundantly and substantially continuously forms attractive, cup-shaped, deep pink blossoms,
(b) exhibits a very bushy and climbing growth habit,
(c) forms vigorous vegetation,
(d) forms attractive, ornamental, semi-glossy, medium green foliage, (e) exhibits excellent disease resistance, particularly with respect to black spot, rust and mildews, and
(f) is well suited for providing attractive ornamentation.

A new rose variety is provided displaying attractive, cup-shaped, deep pink blossoms combined with substantially continuous blossoming and excellent disease resistance.

The new variety well meets the needs of the horticultural industry. It can be grown to advantage as ornamentation in parks, gardens, public areas, and in residential settings to cover a trellis, arbor, or fence. Accordingly, the plant is particularly well suited for growing in the landscape where a climbing rose plant is desired.

The new variety can be readily distinguished from other climbing roses such as 'Radwin' (U.S. Plant Pat. No. 19,310) in that the new variety exhibits a bloom color that is deep pink as opposed to the red colored blossoms of the 'Radwin' variety.

The new variety can also be distinguished from another climbing rose such as 'Margaret Mae' (U.S. Plant Pat. No. 20,953) in that 'Margaret Mae' displays many more petals, upwards of 70-80 petals, versus only 18 petals on the new variety.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radwire', and will be marketed under the Highwire Flyer™.

BRIEF DESCRIPTION OF THE PHOTOGRAPHS

The accompanying photograph shows, as nearly true as it is reasonably possible to make the same in a color illustration of this character, typical blossoms of the new variety. The rose plant of the new variety illustrated herein was approximately three years of age and was grown outdoors on its own roots in West Grove, Pa., U.S.A. when it was observed in June 2015.

FIG. 1 shows a close view of the blossoms and foliage of the new variety.

DETAILED BOTANICAL DESCRIPTION

The chart used in the identification of colors is that of The Royal Horticultural Society (R.H.S. Colour Chart—2015 Edition), London, England. The description is based on the observation of two-year-old specimens of the new variety during June while growing in ground on their own roots at West Grove, Pa., U.S.A.

Class: Climbing Rose.

*Variety*.—'Radwire'.

Plant:

*Height*.—Commonly up to approximately 1.8 m on average of growth.

*Width*.—Commonly approach approximately 90 cm on average.

*Habit*.—Very bushy and climbing.

Branches:

*Stem length*.—Main stems commonly approximately 60-70 cm on average, and secondary stems commonly approximately 25 cm on average.

*Stem color*.—Near Yellow-Green Group 144A mixed with Greyed-Red Group 181A on young stems, and commonly near Yellow-Green Group 144A on old wood.

*Thorns*.—Size: commonly approximately 8 mm in length on average and approximately 4 mm in width on average at the point of attachment when young, and approximately 1 cm in length on average and approximately 7 mm in width on average at the point of attachment when old. Color: commonly near Greyed-Red Group 180A on young stems, and near Greyed-Orange Group 176A when old. Average number on the stem: many.

Leaves:

*Size*.—Commonly approximately 13 cm in length on average, and approximately 9 cm in width on average for a five-leaflet leaf.

*Petiole*.—Length: approximately 2.4 cm on average. Surface texture: upper surface is commonly glabrous to slightly glandular and under surface is commonly glabrous. Color: near Green Group 137C.

*Petiole rachis*.—Length: approximately 7.7 cm on average. Surface texture: upper surface is commonly glabrous to slightly glandular and under surface is commonly glabrous. Color: near Green Group 137C.

*Stipule*.—Size: approximately 1.5 cm in length on average. Color: near Green Group 137C.

*Leaflets*.—Number 3, 5, and 7. Length: approximately 4.5 cm on average for a terminal leaflet, and approximately 2.5 cm on average for a lower leaflet. Width: approximately 4 cm on average for a terminal leaflet, and approximately 2 cm on average for a lower leaflet. Shape: generally ovate with broadly acute apex and rounded base. Margins: serrate. Texture: generally smooth on the upper and under surfaces. Color: (when young): Upper surface: near Yellow-Green Group 146A. Under surface: near Yellow-Green Group 146A blended with Greyed- Red Group 178A. Color (when fully mature): Upper surface: near Green Group 137A. Under surface: near Green Group 137C.

Inflorescence:

*Number of flowers*.—Commonly singly or in a cluster of approximately 2 to 6 blossoms on average per stem, and commonly with approximately 50 blossoms on average being present on the plant at a given time.

*Peduncle*.—Near Yellow-Green Group 144A in coloration, commonly approximately 3.5 cm in length on average, approximately 5 mm in diameter on average, and commonly sparsely covered with small flexible thorns less than 2 mm in length.

*Sepals*.—Upper surface: covered with short pubescence, and commonly near Green Group 138B in coloration. Under surface: commonly puberulent, and commonly near Yellow-Green Group 144A in coloration. Size: commonly approximately 3 cm in length on average, and approximately 1.1 cm in width at the base. Shape: apex is acute with a few foliaceous appendages and base is truncate. Margin: entire, and commonly with an extension on two or three of the sepals measuring approximately 5 mm in length on average and approximately 1 mm in width on average. Number: five.

*Buds*.—Shape: generally ovoid. Length: approximately 2 cm on average as the calyx breaks. diameter approximately 1.5 cm on average as the calyx breaks. Color: when opening near Red Group 45C.

*Flower*.—Form: semi-double, cuplike. Diameter: commonly approximately 10.5 cm on average when fully open. Height: approximately 4.0 cm on average. Color (when opening begins): Upper surface: near Yellow Group 4C at the point of attachment transitioning to near Red-Purple Group N66B towards the apex. Under surface: near White Group 155A at the point of attachment transitioning to near Red-Purple Group 62A towards the apex. Color (at full bloom): Upper surface: near Red-Purple Group N66D and near Yellow-Orange Group 19D at the point of attachment. Under surface: near Red-Purple Group 73D and near Yellow-Orange Group 19D at the point of attachment. Color (at end of blooming): Upper surface: near White Group NN155A at the point of attachment transitioning to near Red-Purple Group 63B towards the apex. Under surface: near White Group 155B at the point of attachment transitioning to near Red Group 55B towards the apex. Fragrance: very slight. Petal number: commonly approximately 18 on average under normal growing conditions. Petal length: commonly approximately 5 cm on average. Petal width: commonly approximately 5.5 cm on average. Petal shape: broadly obovate. Petal margin: entire. Petal apex: slightly cuspidate. Petal base: cuneate. Petal drop: good. Stamen number:

approximately 80 on average. Anthers: number approximately 80 on average and commonly near Yellow-Orange Group 22A in coloration. Filaments: approximately 1 cm in length, and the coloration is near Yellow-Orange Group 21B. Pollen: commonly present in a moderate quantity, and near Yellow-Orange Group 21A in coloration. Pistils: separate and free, and commonly number approximately 45 on average. Styles: commonly approximately 5 mm in length and near White Group NN155A in coloration. Stigma: commonly approximately 1 mm in diameter on average, and near Yellow Group 6A in coloration. Receptacle: commonly substantially round in shape, approximately 9 mm in diameter, smooth in texture, near Yellow-Green Group 144A in coloration, and with achenes commonly being present on the bottom and wall. Hips/seed: not observed to date.

Development:

*Vegetation*.—Medium green vigorous, and strong.

*Blossoming*.—Abundant and substantially continuous from spring to frost.

*Lastingness of flowers*.—Approximately 5 days.

*Resistance to diseases*.—Excellent, particularly with respect to black spot, rust, and mildews. Plants of the 'Radwire' variety have not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following combination of characteristics:

(a) abundantly and substantially continuously forms attractive cup-shaped deep pink blossoms, (b) exhibits very bushy and climbing growth habit, (c) forms vigorous and strong vegetation, (d) forms attractive, ornamental, semi-glossy, medium green foliage, (e) exhibits excellent disease resistance, and (f) is well suited for providing attractive ornamentation; substantially as herein shown and described.

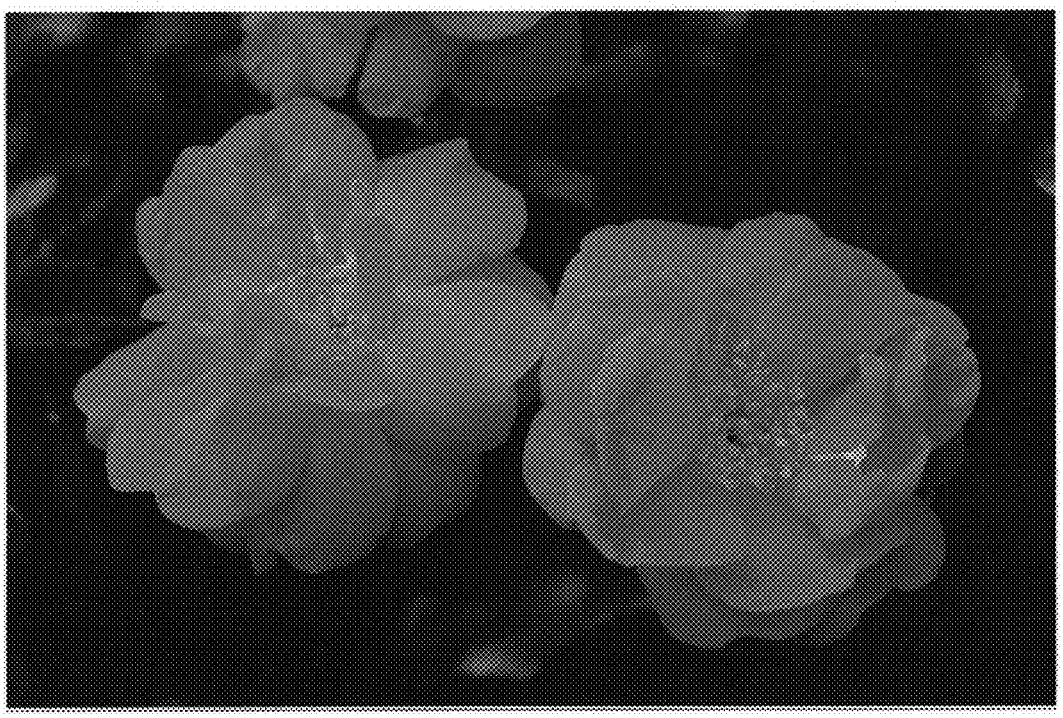

* * * * *